United States Patent [19]
Fathi et al.

[11] Patent Number: 5,648,038
[45] Date of Patent: Jul. 15, 1997

[54] SYSTEMS AND METHODS FOR MONITORING MATERIAL PROPERTIES USING MICROWAVE ENERGY

[75] Inventors: Zakaryae Fathi, Cary; Richard S. Garard, Chapel Hill; Jianghua Wei; Michael L. Hampton, both of Raleigh, all of N.C.

[73] Assignee: Lambda Technologies, Raleigh, N.C.

[21] Appl. No.: 531,045

[22] Filed: Sep. 20, 1995

[51] Int. Cl.$^6$ .................... B29C 71/04; B29C 35/08
[52] U.S. Cl. .................... 264/406; 264/490; 264/40.1; 324/634; 324/636; 324/639; 425/135; 425/143; 425/174.4
[58] Field of Search .................... 264/406, 408, 264/490, 489, 40.1; 425/174.4, 135, 143; 324/636, 639, 634

[56] References Cited

U.S. PATENT DOCUMENTS

| | | | |
|---|---|---|---|
| 3,458,808 | 7/1969 | Agdur | 324/58.5 |
| 4,095,475 | 6/1978 | Buckley | 73/628 |
| 4,106,340 | 8/1978 | Hamid | 73/355 R |
| 4,196,332 | 4/1980 | MacKay et al. | 219/10.55 B |
| 4,200,921 | 4/1980 | Buckley | 367/87 |
| 4,617,439 | 10/1986 | Lespinats et al. | 264/489 |
| 4,653,855 | 3/1987 | Birnbach et al. | 350/163 |
| 4,733,165 | 3/1988 | Richardson et al. | 324/58.5 |
| 4,758,803 | 7/1988 | Thomas, III | 331/65 |
| 4,767,902 | 8/1988 | Palaith et al. | 264/432 |
| 4,806,292 | 2/1989 | Delacy | 264/40.1 |
| 4,839,588 | 6/1989 | Jantsch et al. | 324/158 |
| 4,904,928 | 2/1990 | Lewis | 324/636 |
| 4,959,614 | 9/1990 | Bowling et al. | 324/636 |
| 5,008,506 | 4/1991 | Asmussen et al. | 219/10.55 M |
| 5,039,947 | 8/1991 | Kraszewski et al. | 324/634 |
| 5,219,498 | 6/1993 | Keller et al. | 264/40.1 |
| 5,296,271 | 3/1994 | Swirbel et al. | 427/493 |
| 5,321,222 | 6/1994 | Bible et al. | 219/745 |
| 5,331,284 | 7/1994 | Jean et al. | 324/639 |
| 5,397,993 | 3/1995 | Tews et al. | 324/634 |
| 5,453,226 | 9/1995 | Kline et al. | 254/40.1 |
| 5,486,319 | 1/1996 | Stone et al. | 264/406 |

FOREIGN PATENT DOCUMENTS

0326191A2  2/1984  European Pat. Off. .

OTHER PUBLICATIONS

Lauf et al.; *Polymer Curing In A Variable Frequency Microwave Oven*; U.S. Department of Energy; (Jul. 1993).

*Primary Examiner*—Jeffery R. Thurlow
*Attorney, Agent, or Firm*—Bell, Seltzer, Park & Gibson, P.A.

[57] ABSTRACT

Systems and methods for monitoring workpiece and workpiece material characteristics using microwave energy are disclosed. A system includes a chamber, including means for generating variable frequency microwave energy; means for positioning a workpiece within the chamber; means for subjecting the workpiece to a plurality of different microwave frequencies; and means for monitoring characteristics of the workpiece. One or more characteristics of a workpiece, or workpiece material, may be monitored by positioning the workpiece within a chamber having means for generating variable frequency microwave energy; subjecting the workpiece to microwave irradiation at a plurality of frequencies; detecting power reflection for each one of the plurality of microwave frequencies to provide power reflection data; and comparing the power reflection data to a predetermined set of power reflection data. The result of signature analysis can be coupled with a product process controller to achieve a real-time feedback control on monitoring and adjusting of process parameters.

25 Claims, 15 Drawing Sheets

SYSTEMS AND METHODS FOR MONITORING MATERIAL PROPERTIES USING MICROWAVE ENERGY

FIELD OF THE INVENTION

The present invention relates generally to microwave energy, and more particularly to monitoring material properties using microwave energy.

BACKGROUND OF THE INVENTION

Microwave energy is being used increasingly in a variety of manufacturing operations, especially those involving the curing of polymeric materials. Microwave processing of polymeric materials is advantageous for a number of reasons. The application of microwave irradiation decreases the time required to cure some polymers as compared with conventional heating methods. This is because the volumetric deposition of microwave irradiation is more efficient than conduction from the surface resulting from conventional heating techniques. See, for example, *Polymer Curing In A Variable Frequency Microwave Oven*, R. J. Lauf et al., Oak Ridge National Laboratory. See also, U.S. Pat. No. 5,296,271 to Swirbel et al., which proposes a method of curing photoreactive polymers by exposing them to microwave irradiation. Additionally, microwave processing is more economically attractive than conventional heating techniques due to the shorter processing time required to cure the resin.

The quality of a resin product is dependent on, among other things, adequate resin flow, gelation, pressure, temperature and cure rate. Unfortunately, it is difficult to determine whether these parameters have been adequately achieved during many processes such as molding or curing. This is because the product typically is hidden from view during processing, and because the manifestation of inadequate processing, can only be detected if the interior of the resin product can be viewed. It is desirable, therefore, to be able to perform diagnostic tests on resin products during manufacturing to determine various information about the physical and chemical state that is otherwise obscured from view.

It is known to use microwave energy for measuring various characteristics or properties of materials, including moisture content, thickness, magnetic anisotropy, and dielectric anisotropy. For example, U.S. Pat. No. 3,458,808 to Agdur discloses an apparatus for measuring various properties of a material via microwave resonance techniques and measuring the time interval between the resonant frequency peaks of a single mode microwave cavity. U.S. Pat. No. 4,904,928 to Lewis, discloses measuring variations in material properties by observing changes in the resonant frequency of various modes, relative to one another, within a single mode microwave cavity.

Unfortunately, resonance techniques are able to monitor only characteristics or properties within a localized area of a product. Furthermore, techniques based on the resonance condition of a microwave cavity cannot generate information about an entire product. However, it is desirable to obtain volumetric information about various properties of a workpiece during the manufacturing process. It is also desirable to provide real-time feedback of these properties to enable greater control over manufacturing and fewer rejected products during manufacturing.

SUMMARY OF THE INVENTION

It is an object of the present invention to utilize microwave energy to monitor volumetrically a plurality of material properties during and or after processing.

It is another object of the present invention to provide non-destructive measurement of material characteristics and properties during manufacturing of a product.

These and other objects are provided, according to the present invention, by systems and methods for monitoring a workpiece using microwave energy. Such a system may comprise a chamber, including means for generating variable frequency microwave energy; means for positioning a workpiece within the chamber; means for subjecting the workpiece to a plurality of different microwave frequencies; and means for monitoring a characteristic of the workpiece. In particular, means for monitoring a characteristic of a workpiece comprises means for detecting the power reflection for each one of the plurality of launched microwave frequencies to provide power reflection data; and means for comparing the power reflection data to a first predetermined set of power reflection data. The term "workpiece characteristic" comprises the physical and/or chemical state of the workpiece and workpiece material. For example, the workpiece may comprise a resin and the characteristic monitored may be the degree of cure of the resin, workpiece density, and the presence of defects. Each workpiece reflection curve is directly related to the dielectric properties of the workpiece, which in turn is related to these various workpiece characteristics.

Monitoring means may be used to monitor a single characteristic about the workpiece, or a plurality of characteristics, either simultaneously or sequentially. Means for storing power reflection data, and means for generating a signature curve for a workpiece by plotting the power reflection data as a function of microwave frequency, may also be provided.

A system, according to the present invention, may further comprise means for identifying a workpiece having power reflection data that does not fall within an acceptable range of power reflection data. This may comprise comparing the signature curve of a workpiece with the signature curve of a workpiece having known chemical and physical conditions. The identification of workpieces with reflection data not within an acceptable range may be performed at any time during manufacturing or processing, including before, during, and after microwave processing.

According to another aspect of the invention, a method is provided for monitoring one or more characteristics of a workpiece, or workpiece material, comprising the steps of: positioning a workpiece within a chamber having means for generating variable frequency microwave energy; subjecting the workpiece to microwave irradiation at a plurality of frequencies; detecting power reflection for each one of the plurality of microwave frequencies to provide power reflection data; and comparing the power reflection data to a predetermined set of power reflection data. Optionally, power reflection data may be stored, for example, within a computer, and used for generating a signature curve for the workpiece by plotting the power reflection data as a function of microwave frequency. An additional step of identifying a workpiece having power reflection data that does not fall within an acceptable range of power reflection data may be provided.

A plurality of different characteristics of a single workpiece may be monitored by comparing the power reflection data with a plurality of predetermined sets of power reflection data. Similarly, one or more characteristics of a plurality of workpieces may be monitored. The step of identifying a workpiece having power reflection data that does not fall within an acceptable range of power reflection data may be performed during the processing step.

DETAILED DESCRIPTION OF PREFERRED EMBODIMENTS

Figure 1:
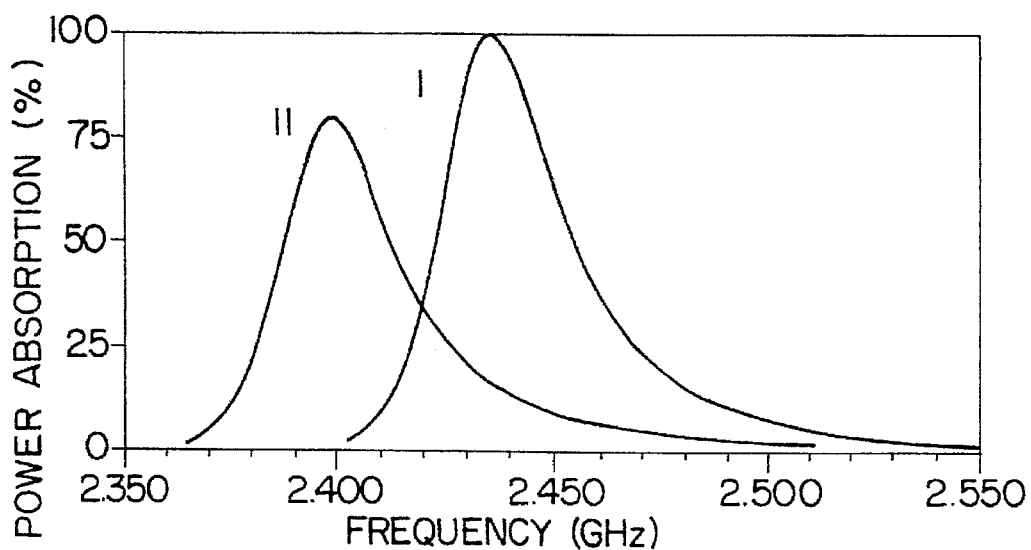
FIG. 1 illustrates the resonant peaks of a single-mode microwave cavity with and without a workpiece therein.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the thickness of layers and regions may be exaggerated for clarity. Like numbers refer to like elements throughout.

When a workpiece is irradiated with microwave energy within a microwave cavity, the interaction between the microwave energy and the workpiece is influenced by the applied microwave frequency, cavity dimensions, workpiece configuration, workpiece material properties, and the location of the workpiece within the cavity. This interaction can be monitored using the percentage of the power reflected back to the microwave launcher. This percentage is calculated by dividing the reflected power ($P_r$) by the input power ($P_i$). When a workpiece is irradiated with a range of frequencies from a variable frequency microwave source, for example 1 to 20 GHz, a power reflection curve as a function of incident frequencies can be obtained. The shape of this curve comprises intrinsic peaks that are related to the dielectric properties, shape, and configuration of the workpiece material.

For every workpiece in a given position within a microwave cavity, there is a unique curve, or "signature curve", over the launched microwave frequency range. Any variation in this signature curve, as indicated by frequency shift and/or magnitude change of the intrinsic peaks, is solely a function of changing material properties or conditions. For example, if the dimensions of a microwave cavity are held constant, and two workpieces, comprised of the same material and having substantially identical shapes and sizes, are positioned within the cavity in substantially the same way, the signature curves generated for each workpiece, upon being irradiated with the substantially same range of microwave frequencies, will be substantially identical. Any variation between the two signature curves is an indication that the workpieces do not comprise material in the same condition or state. For example, one workpiece may not be in a fully cured state, or one workpiece may have an imperfection, such as a cavity caused, for example, by an air bubble entrained during molding.

The behavior of an intrinsic peak in a single mode microwave cavity containing a workpiece illustrates the material/microwave interaction. FIG. 1 illustrates a typical shift of a resonant peak at 2.45 GHz within a single-mode, cylindrical cavity before and after loading of a workpiece. Curve I is the intrinsic peak representing the resonant mode at 2.45 GHz (100% power absorption at 2.45 GHz) inside the cavity. When the cavity contains a workpiece, the peak frequency and power absorption percentage of the peak will shift as illustrated by Curve II. The magnitude of the shift depends on the shape, dielectric properties, and location of the workpiece within the cavity.

Figure 2:
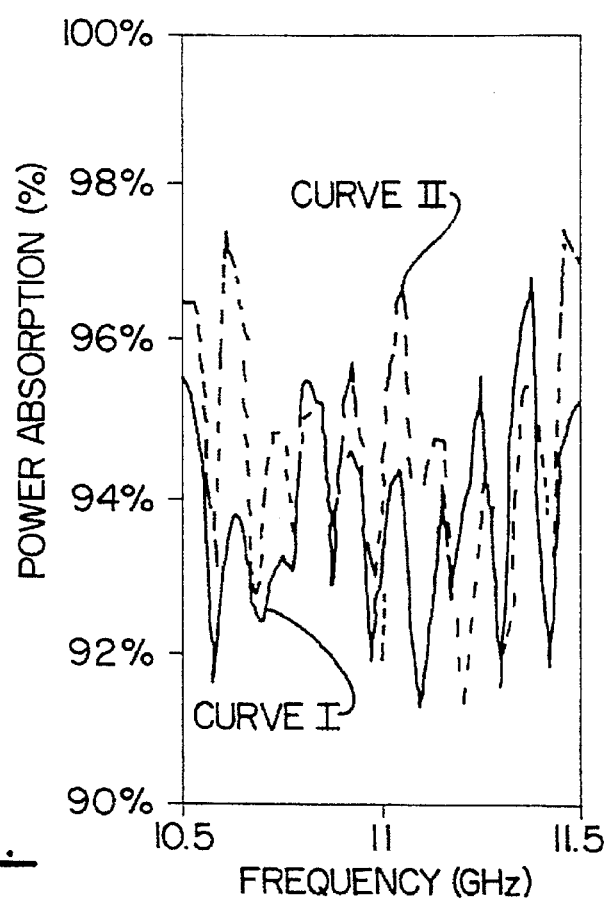
FIG. 2 illustrates the signature curves for a workpiece at two different stages of cure in a multimode cavity.

Referring now to FIG. 2, signature curves generated in a multimode cavity comprise a plurality of intrinsic peaks. Illustrated are the power absorption curves for an epoxy/glass workpiece irradiated by sweeping it with microwave energy between 10.5 and 11.5 GHz at two stages: fully cured and 75% of full cure. Curve I (solid line) is the signature curve for the workpiece in a state of 75% cure, and Curve II (dotted line) is the signature curve for the fully cured workpiece. As shown, the intrinsic peaks of Curve I shifted, both in frequency and magnitude, as a result of differences in the state of cure. As those with skill in the art would understand, the term "sweeping", as used hereinafter, refers to exposing a workpiece to many of the microwave frequencies within a particular range. Frequency sweeping results in uniform irradiation because many cavity modes can be excited. Sweeping may be accomplished by launching the different frequencies within a range either simultaneously, or sequentially.

Because dielectric properties of a polymeric material are dependent upon the temperature and degree of cure, any shift of the intrinsic peaks of a signature curve is closely related to the change in temperature and stage of cure. Also, because the temperature and stage of cure is determinative of the resin viscosity for any given composite material, a signature curve shift may be used to determine viscosity changes during the stages of cure. Consequently, both the stage of cure and viscosity of a polymeric material is determinable from signature curve shifts. As would be understood by those having skill in the art, it is not necessary to produce signature curves in printed form or on a computer screen. Intrinsic peak shifts can be calculated and product characteristics determined independent of a tangible signature curve. The power reflection data necessary to produce a signature curve may simply be analyzed within a processor, such as a computer.

Tremendous advantages are offered by the present invention because of the ability to monitor, in-situ, the chemical and physical condition of a resin during processing. Most curing of polymeric materials takes place within an autoclave wherein precise application of pressure cycles is extremely important. By monitoring a workpiece in-situ, the pressure cycle can be applied at the precise point in time and in the exact amount to achieve the optimum property characteristics desired in the final workpiece. Furthermore, because polymeric materials are generally transparent or semi-transparent to microwave energy, volumetric monitoring of a workpiece is possible. As used hereinafter, the term "volumetric monitoring" refers to the ability to interrogate an entire workpiece with a plurality of different microwave frequencies within a given range. By contrast, existing microwave techniques are capable of monitoring only select regions of a workpiece.

Another advantage of the present invention is that when the frequency ranges of the intrinsic peaks of a workpiece are within the frequency ranges utilized for curing the workpiece material, the same variable frequency microwave source can be used for both curing and monitoring. However, heating and monitoring can be provided by separate microwave sources. Additionally, the present invention may be utilized even where curing or the addition of heat is not required. Low power microwave energy can be used to monitor a workpiece without causing excessive or destructive heating.

The present invention can be utilized as an intelligent processing quality assurance and control technique. For example, when variable frequency microwave energy is launched within an autoclave containing a polymer, the signature curve will vary at different cure stages and when variations or defects are present. Once a signature curve is obtained for a workpiece of known quality, subsequent workpieces can be monitored and their signature curves compared with this curve. Through the use of a computer, signature curve analysis can be performed during manufacturing and unsatisfactory workpieces can be identified before further processing is performed, thereby saving time, money and materials. Furthermore, the intelligent processing system can be used to optimize process cycles by giving feedback on the stage of cure during processing. The ability to monitor the stage of cure permits precise control over temperature and pressure, thereby increasing efficiencies, increasing the production rate, and reducing the number of rejects.

Figure 3A:
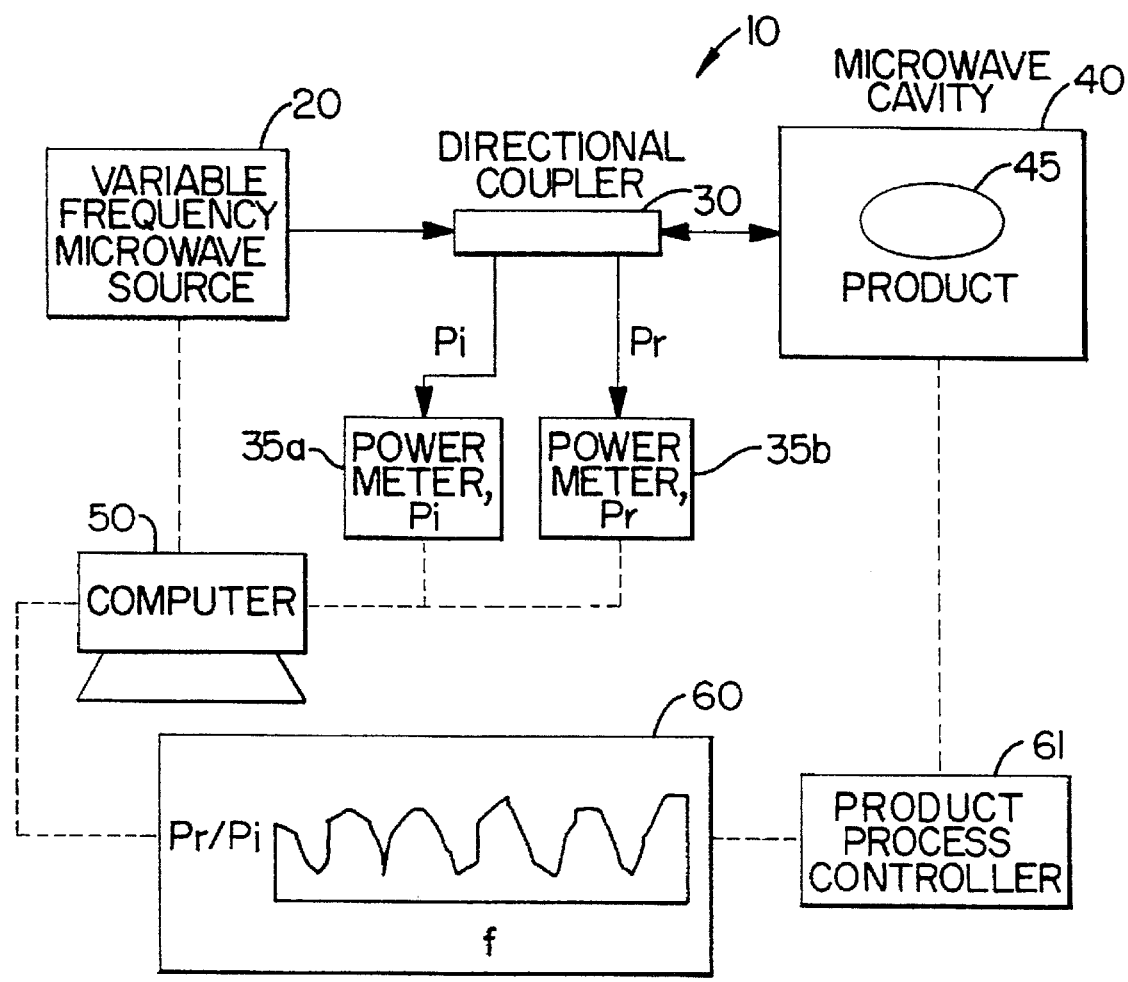
FIG. 3A, 3B are schematic illustrations of systems for generating variable frequency microwaves, analyzing power reflection data, and providing real-time feedback to the process, according to the present invention.
Figure 3B:
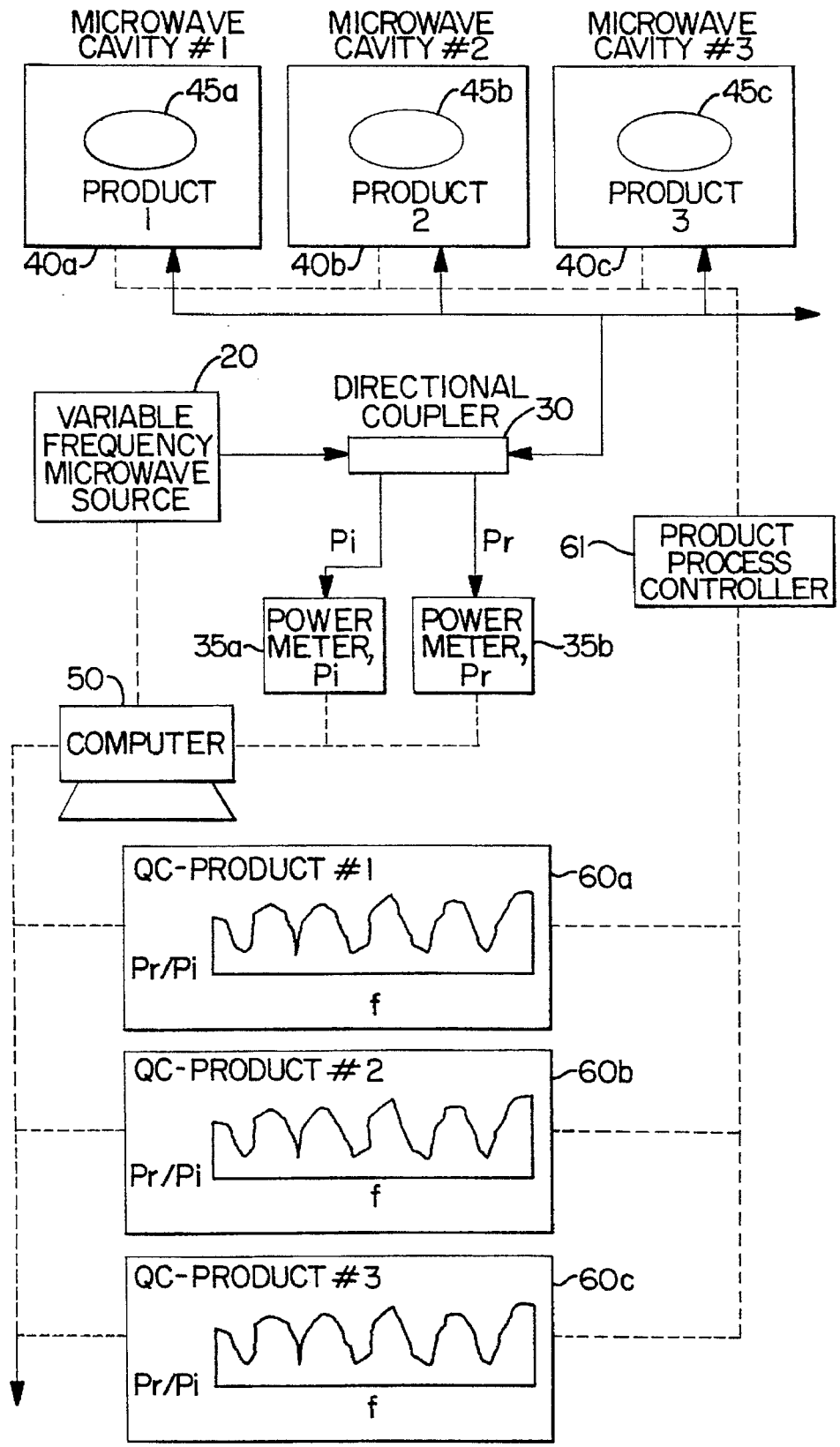

Referring now to FIG. 3A, a system for generating signature curves for a workpiece irradiated with variable frequency microwave energy, according to the present invention, is schematically illustrated. The system 10 comprises a variable frequency microwave source 20, a directional coupler 30 and power meters 35a,35b to measure the input power and reflected power, a microwave cavity 49 to host the workpiece 45, and a computer 50 to generate, analyze and compare power reflection data 60. Once a decision is made on the status of the product (workpiece), the computer will send an action command to a product process controller 61 to carry out proper actions regarding the product. The action could be, but is not limited to, a pass/fail marker or adjustment of process conditions such as temperature, pressure, and various other parameters. The system 10, illustrated in FIG. 3A can also be configured to generate signature curves for multiple products, either sequentially or simultaneously. As illustrated in FIG. 3B, multiple workpieces 45a,45b,45c can be hosted within multiple microwave cavities 40a,40b,40c. The computer 50 generates, analyzes, and compares the power reflection data 60a,60b,60c for each workpiece. Once decisions are made on the status of products (workpieces), the computer will send action commands to a combined or individual product process controller 61 to carry out proper actions regarding the products.

The function of the computer 50 is to recognize the characteristics of a material at different stages by comparing the real-time power reflection curve with a database. The database contains the power reflection signatures of the material of given status under various conditions. Once a match is found between the real-time power reflection curve and the signature curve based on the predetermined tolerance or fuzzy logic, the computer will send an action command to the product process controller. This signature analysis may be performed periodically or simultaneously on the product.

The variable frequency microwave source can be a signal generator with a traveling wave tube (TWT) or other means, including a low power solid state oscillator. The power level from the source is dependent on the particular application. The microwave cavity preferably comprises metallic walls, and may have any shape desired. Furthermore, the cavity may be configured as a single or multi-mode cavity. An exemplary variable frequency microwave source, directional coupler, and cavity is described in U.S. Pat. No. 5,321,222, to Bible et al., the disclosure of which is incorporated herein by reference in its entirety.

In general, a microwave signal generator or microwave voltage-controlled oscillator generates a low-power microwave signal for input to the microwave cavity. A first amplifier may be provided to amplify the magnitude of the signal output from the microwave signal generator or the microwave voltage-controlled oscillator. A second amplifier is provided for processing the signal output by the first amplifier. A power supply is provided for operation of the second amplifier. A directional coupler is provided for detecting the direction of a signal and further directing the signal depending on the detected direction. Preferably a high-power broadband amplifier, such as, but not limited to, a TWT, tunable magnetron, tunable klystron, tunable twystron, and a tunable gyrotron, is used to sweep a range of frequencies of up to an octave in bandwidth spanning the 300 MHz to 300 GHz frequency range.

Attenuators may be used to reduce the power level of the input and reflected power from the directional coupler before reaching the computer 50, depending on the power level from the source. Preferably, power levels used are high enough to generate a signature curve without causing excessive internal heat within the workpiece. However, if heating is desired during the processing of a workpiece, high power variable frequency microwaves may be used for heating and monitoring the workpiece, simultaneously. Alternatively, the microwave source may be configured to launch high power microwave energy to heat a workpiece, and then launch low power microwave energy to monitor the workpiece.

Power reflection data generation, analysis, and storage, as well as signature curve generation, analysis, and storage, is performed by the computer 50. The following examples are illustrative of the advantages and capabilities of the present invention. However, the present invention is not limited to the uses described in the examples. In addition to uses involving polymeric materials, the systems and methods disclosed herein are applicable to any and all materials that are substantially transparent to microwave irradiation.

EXAMPLE 1

Figure 4:
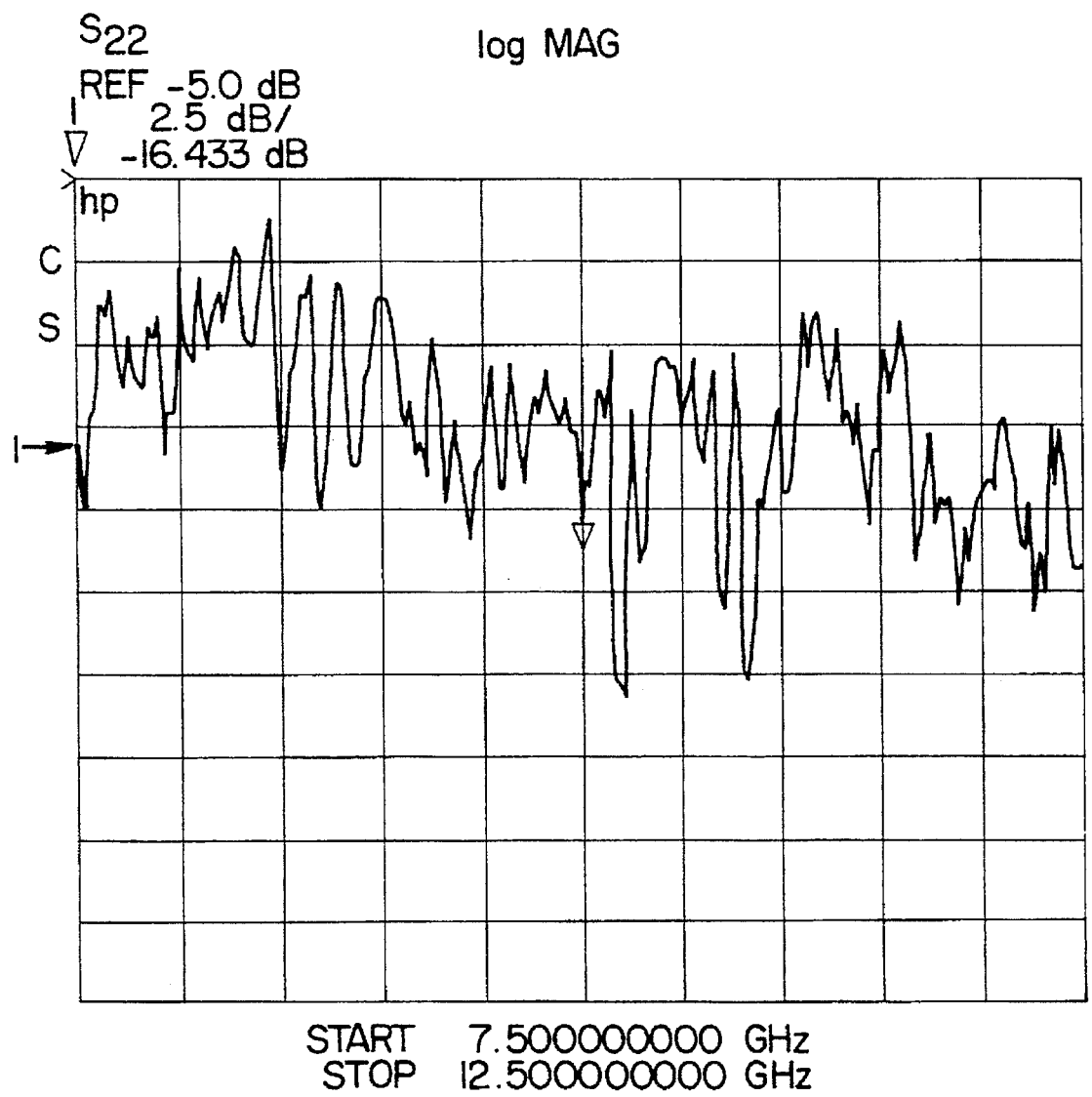
FIGS. 4–15 are signature curves for various workpieces generated according to the present invention.

FIG. 4 illustrates the signature curve for an empty microwave cavity having dimensions of 12"×14"×10" irradiated with variable frequency microwave energy between 7.5 and 12.5 GHz, and wherein the power output from the source is 0 dB. The frequency scale, along the x axis, is from 7.5 to 12.5 GHz with 0.5 GHz intervals. The reflected power scale, along the y axis, is from −30 to −5 dB with 2.5 dB intervals. The input power is the same for all frequencies in the frequency scale. Therefore, the reflected power versus frequency curve is the same as the curve of the reflected power divided by input power versus frequency. These same scales are used consistently throughout the remainder of the examples.

EXAMPLE 2

Figure 5:
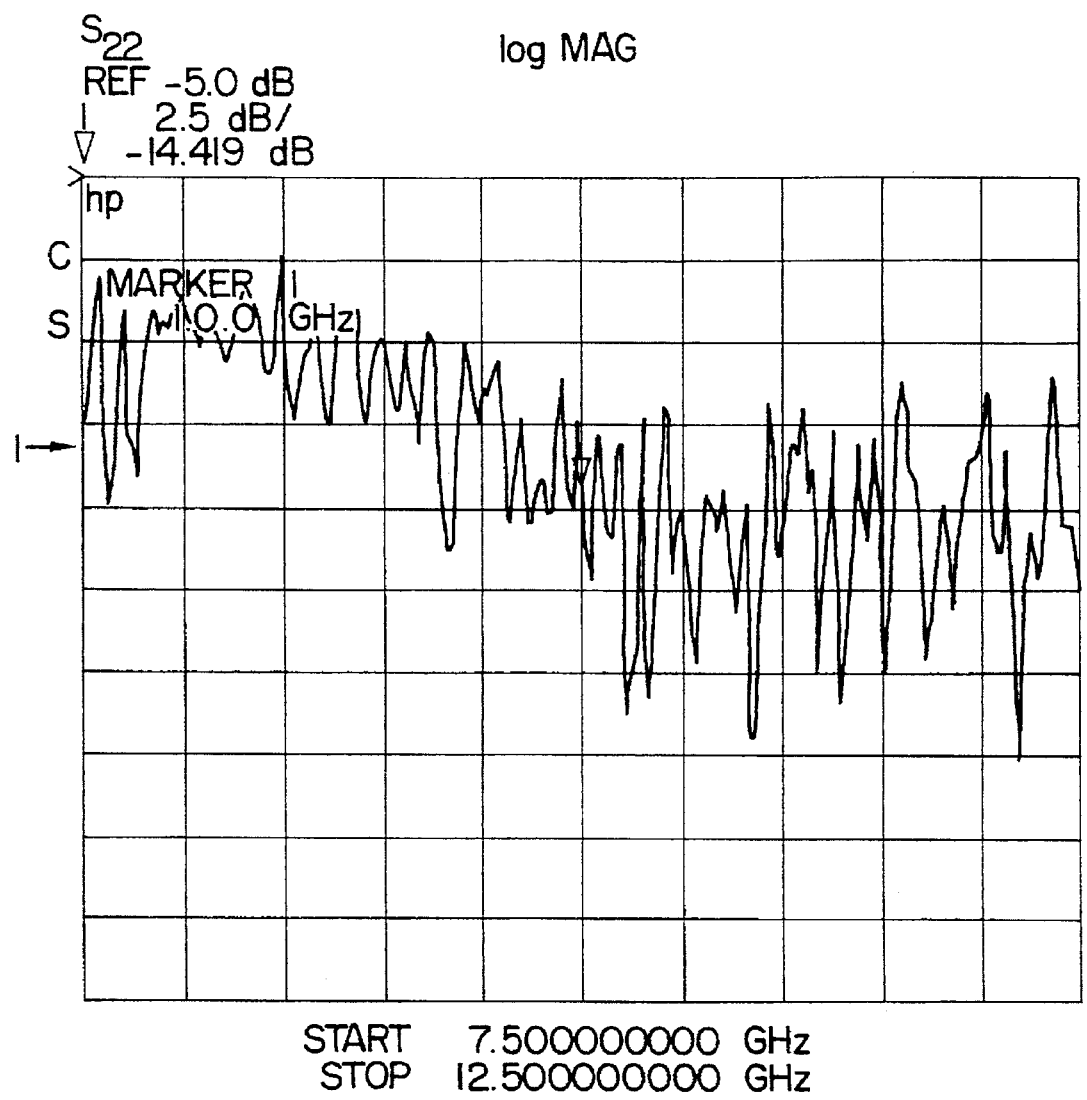

FIG. 5 illustrates the signature curve for an uncured epoxy workpiece positioned at the center of the cavity in Example 1, above, and irradiated with the same range of variable frequency microwave energy (7.5 to 12.5 GHz). The uncured epoxy workpiece has a mass of approximately 60 grams. The intrinsic peaks of the signature curve in FIG. 5 have shifted, both in frequency and magnitude with respect to the signature curve of FIG. 4, thus indicating the presence of the workpiece within the cavity.

EXAMPLE 3

Figure 6:
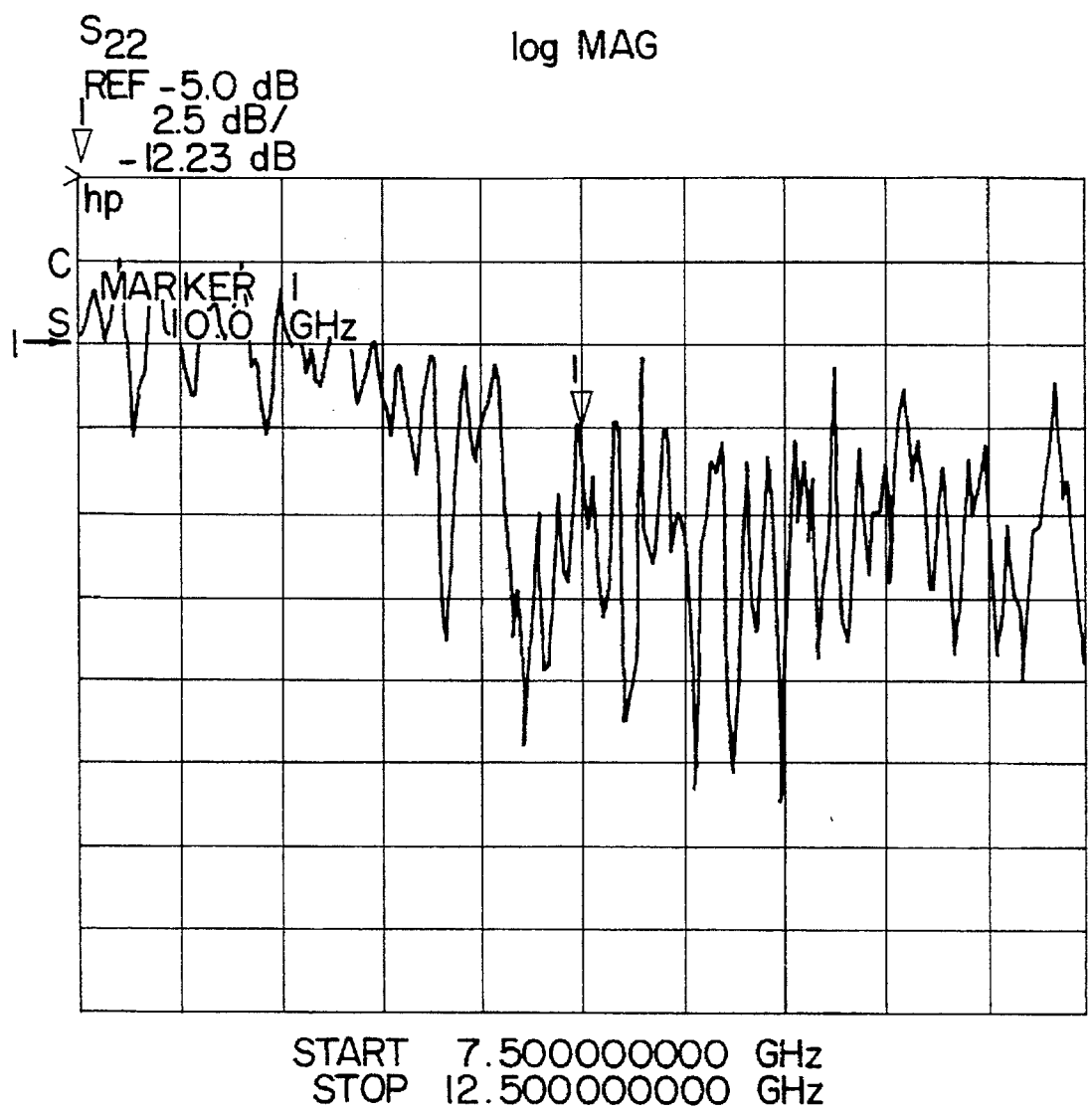

FIG. 6 illustrates the signature curve for the epoxy workpiece of Example 2 after being fully cured. The signature curve was generated under the same conditions as the previous examples (i.e., same position within the same microwave cavity, and same range of variable frequency microwave irradiation). The intrinsic peaks of the signature curve in FIG. 6 have shifted, both in frequency and magnitude, with respect to the signature curve of FIG. 5, indicating the change in the degree of cure. By overlapping the axes of the graphs in FIG. 5 and FIG. 6, the frequency and magnitude shifts of the individual intrinsic peaks can be observed. The computer 50 in FIGS. 3A, 3B compares power reflection data in much the same way. Through calibration using workpieces at known stages of cure, the signature curves for any workpiece can be used to determine the degree of cure during any stage of production.

EXAMPLE 4

Figure 7:
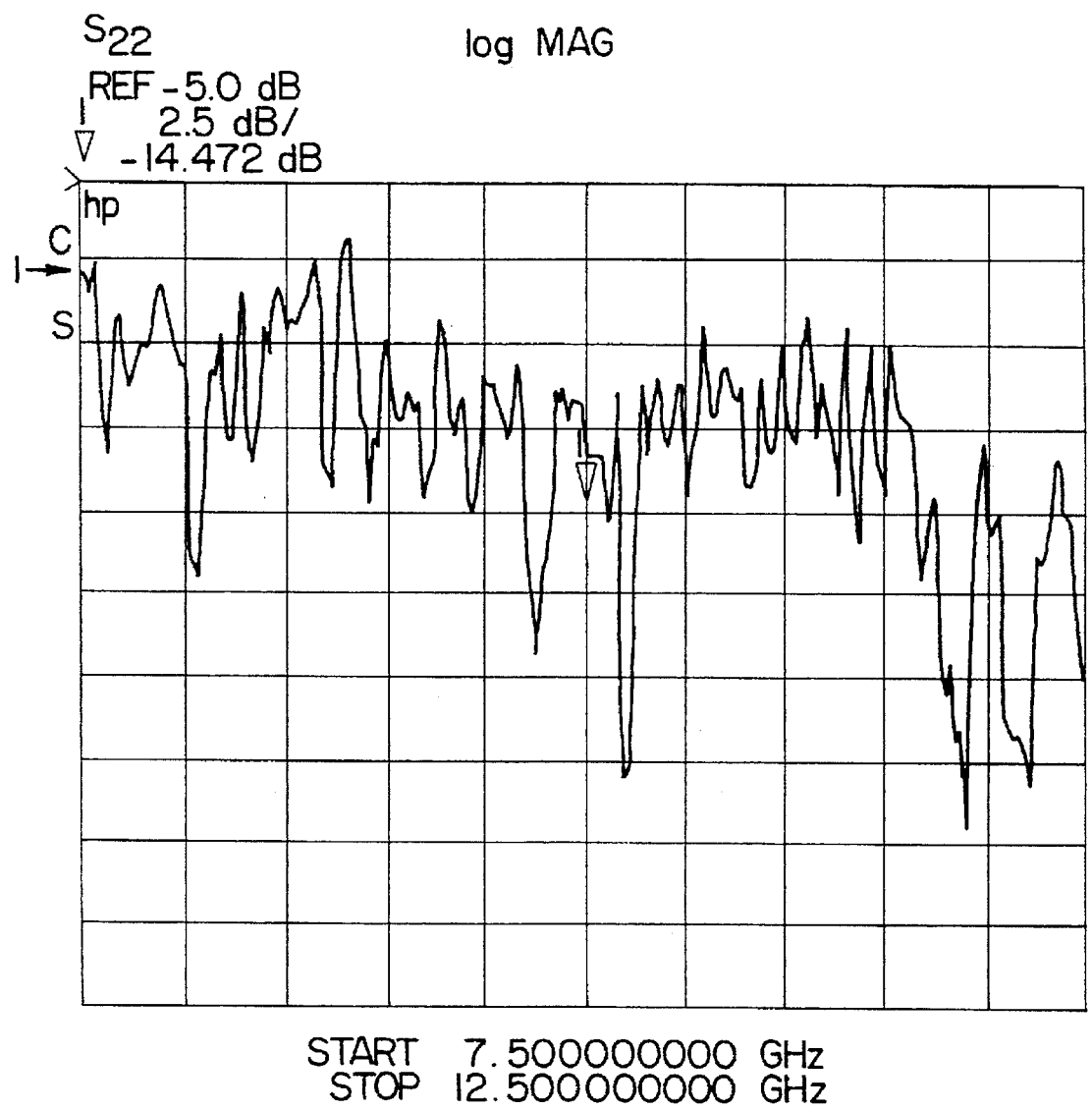

FIG. 7 illustrates the signature curve for an uncured epoxy/glass composite workpiece, having dimensions of about 8"×8"×0.12", in an uncured state. The signature curve was generated by positioning the workpiece in the center of the same microwave cavity used in the above examples, and irradiating the workpiece with the same range of variable frequency microwave energy (7.5 to 12.5 GHz).

Figure 8:
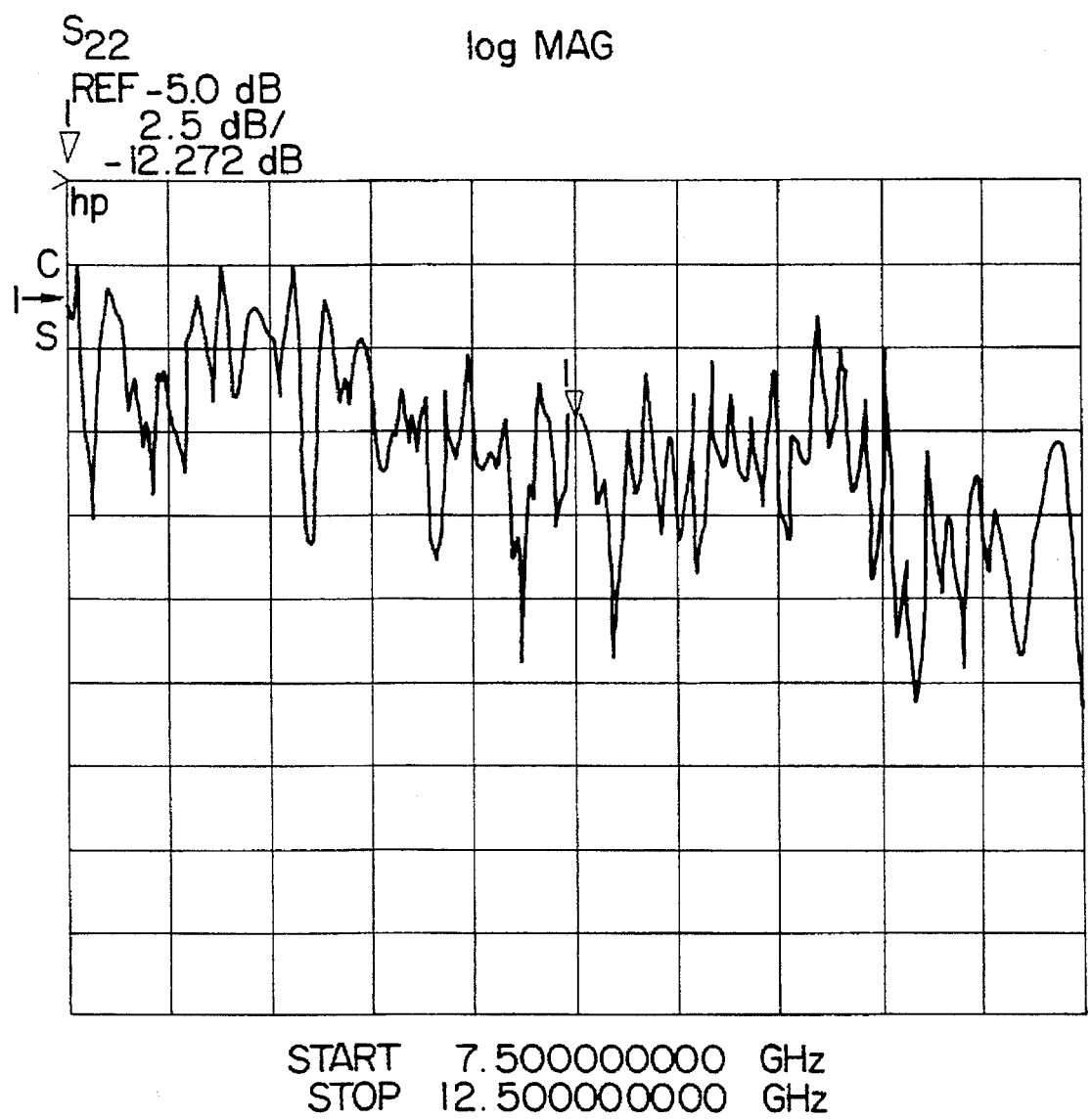

FIG. 8 illustrates the signature curve for the same epoxy workpiece above after being fully cured. The signature curve was generated under the same conditions (i.e., same position within the same microwave cavity, and same range of variable frequency microwave irradiation). The intrinsic peaks of the signature curve in FIG. 8 have shifted, both in frequency and magnitude, with respect to the signature curve of FIG. 7, indicating the change in the degree of cure.

Figure 9:
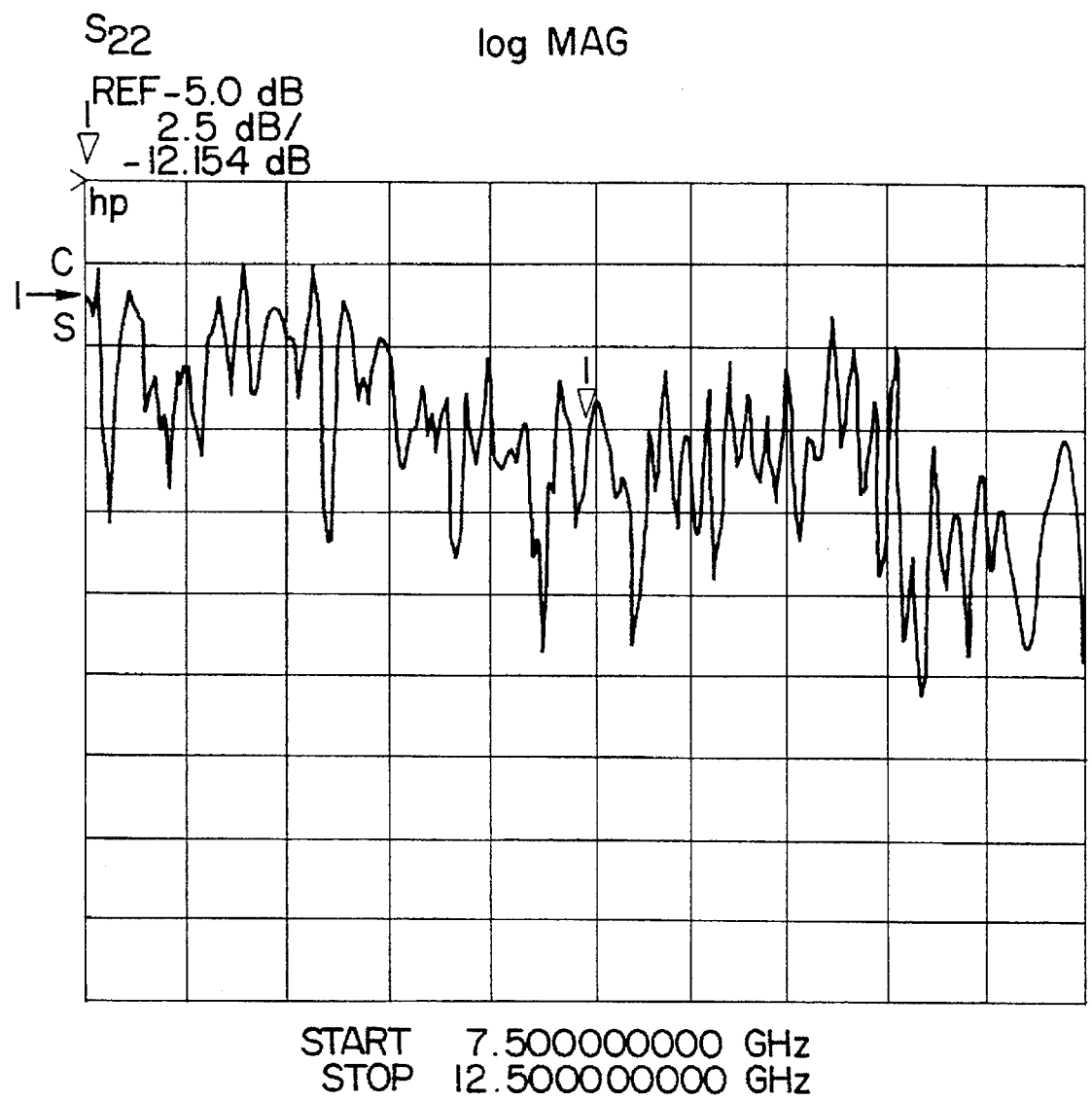

FIG. 9 illustrates the reliability and repeatability of determining the degree of cure of a composite workpiece using signature curves. The same fully cured workpiece above was irradiated with microwave energy in the same range used to produce the signature curve of FIG. 8. The two curves represented by FIG. 8 and FIG. 9 are identical.

EXAMPLE 5

Figure 10:
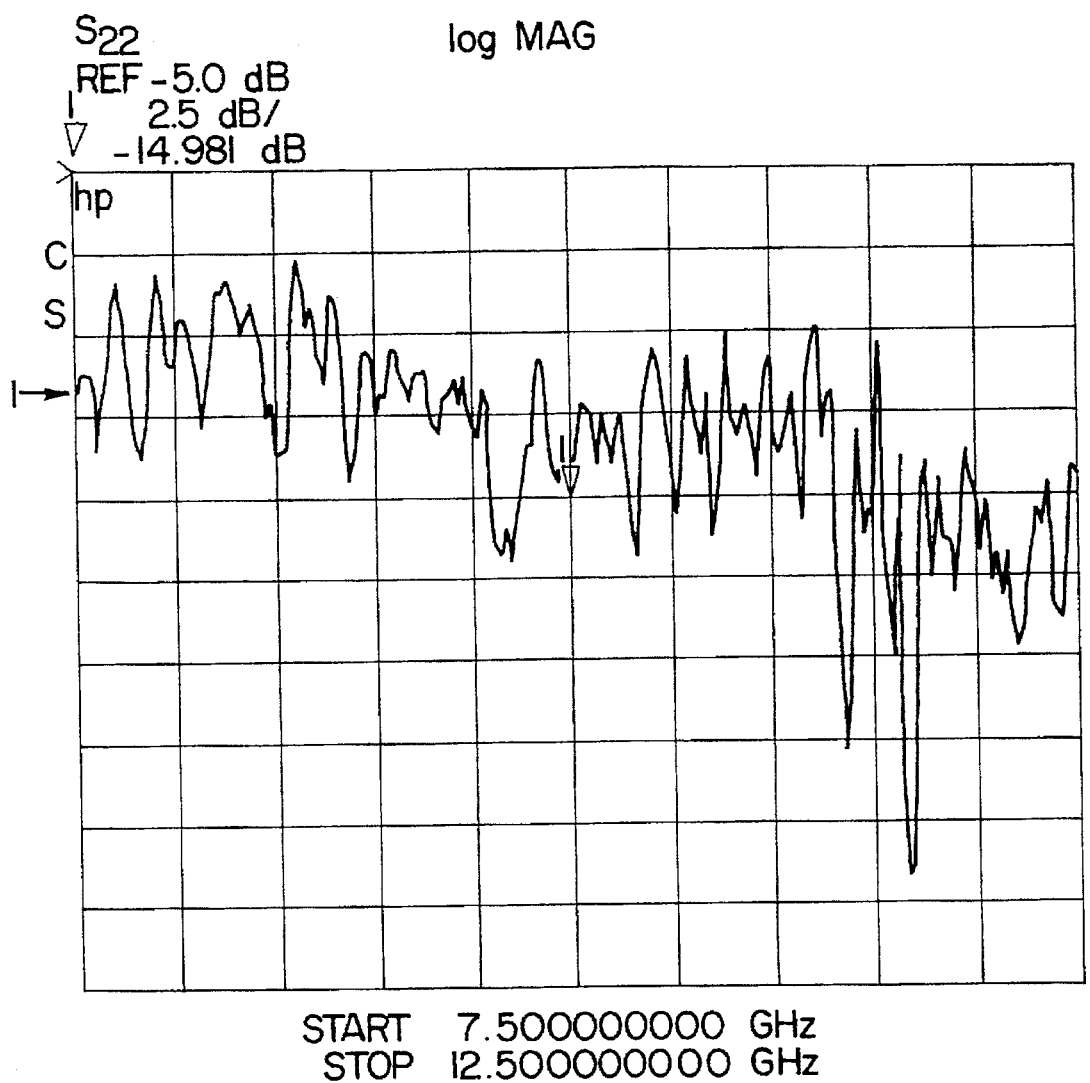
Figure 11:
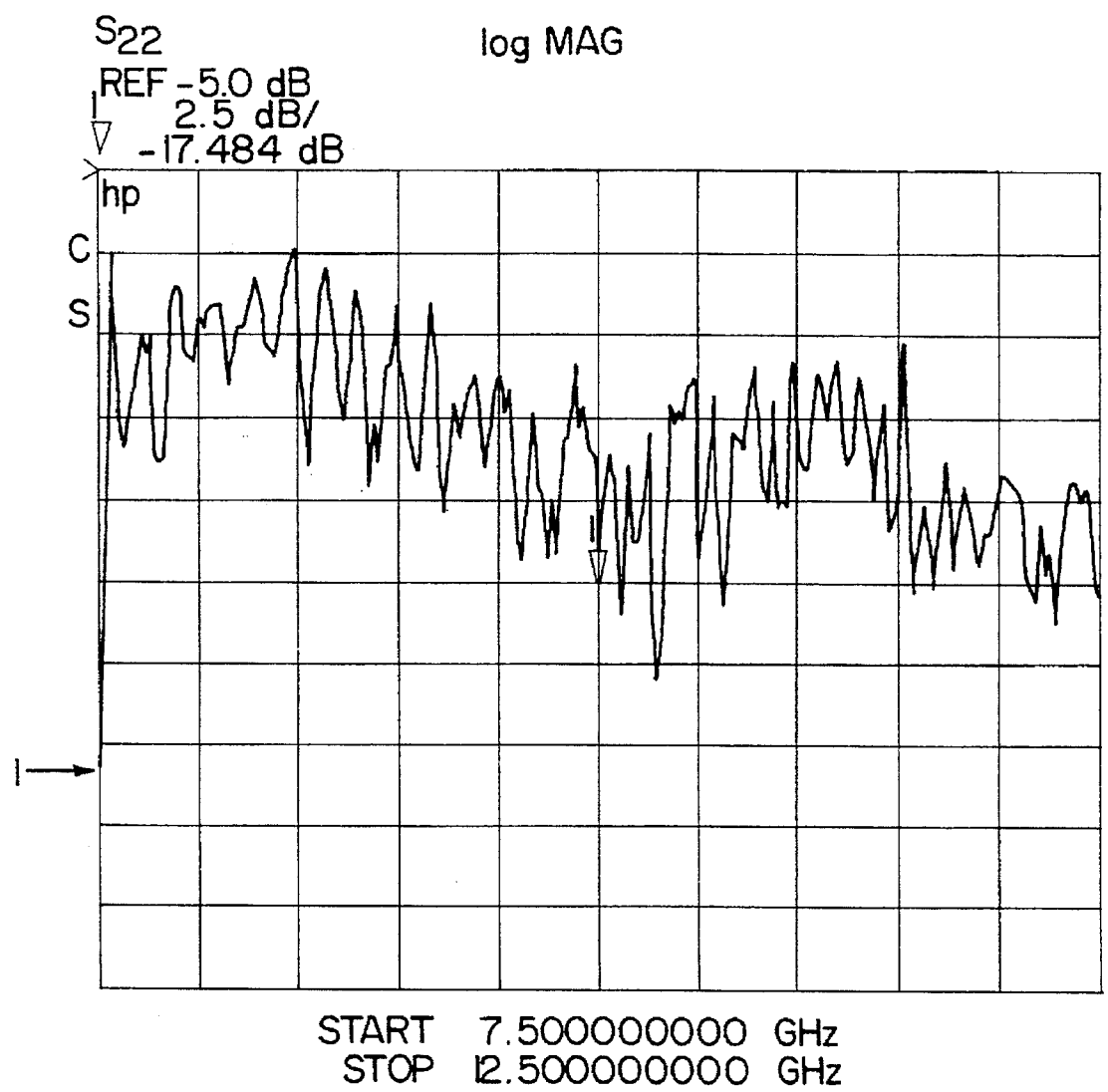

FIG. 10 and FIG. 11 illustrate the effect of the position of a workpiece within a microwave cavity on its signature curve. An 8"×8"×0.12" epoxy/glass composite at a 75% stage of cure was positioned at the center of the microwave cavity described in Example 1, and irradiated with variable frequency microwave energy in the range of 7.5 to 12.5 GHz. A signature curve was generated, as shown in FIG. 10. The same workpiece, in the same 75% stage of cure was positioned away from the center of the cavity, and adjacent a cavity wall. A signature curve was generated, as shown in FIG. 11. The intrinsic peaks of the signature curve in FIG. 11 have shifted, both in frequency and magnitude, with respect to the signature curve of FIG. 10, indicating the effect of location of the workpiece within the cavity.

EXAMPLE 6

Figure 12:
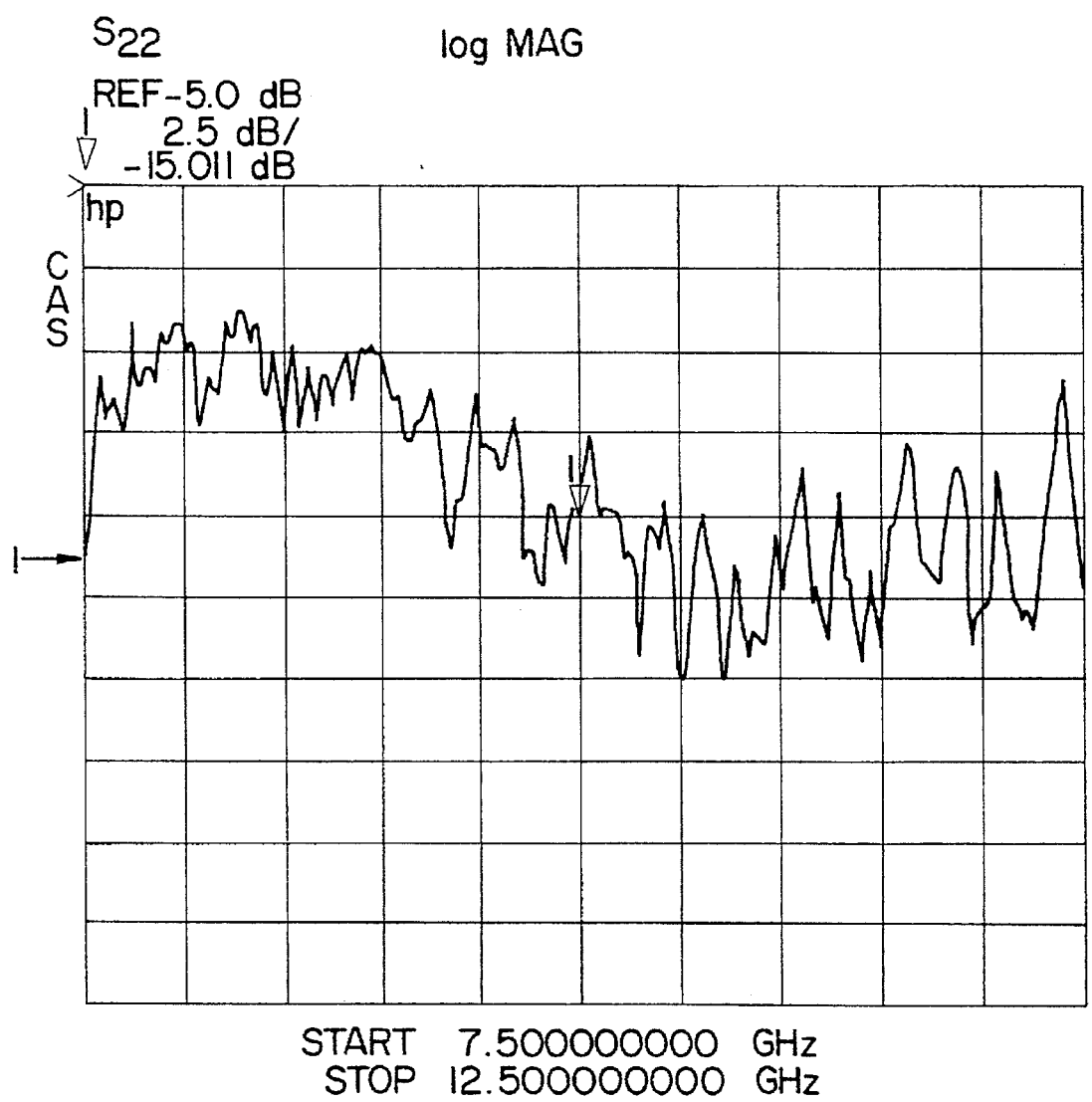
Figure 13:
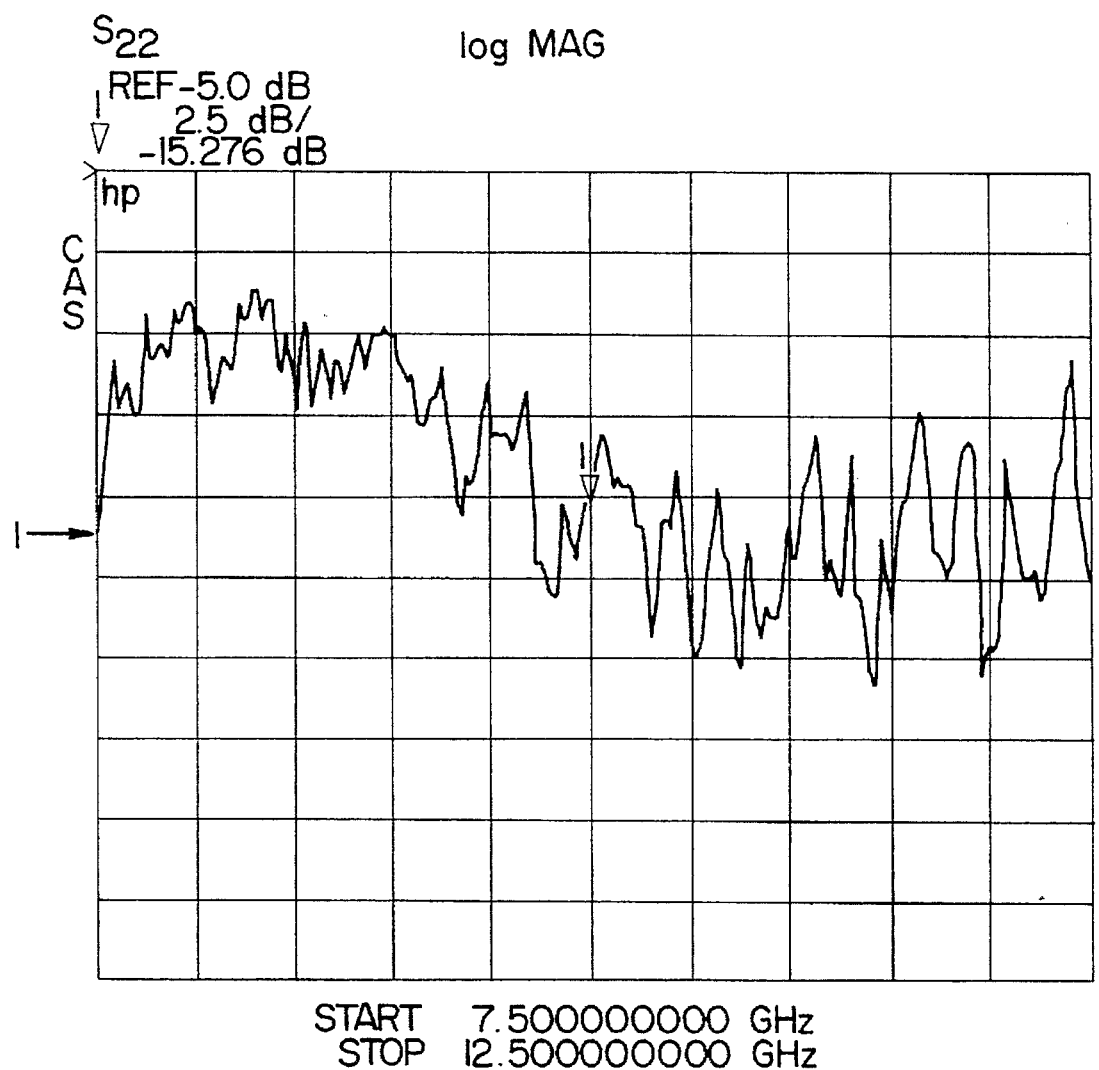

FIG. 12 and FIG. 13 illustrate the effectiveness of the present invention in detecting material imperfections and defects using signature curves. FIG. 12 illustrates the signature curve for a unidirectional graphite fiber/epoxy workpiece positioned at the center of the cavity in Example 1, above, and irradiated with the same range of variable frequency microwave energy (7.5 to 12.5 GHz). The workpiece has dimensions of approximately 3"×3"×0.1" FIG. 13 illustrates the signature curve for a workpiece of the same dimensions and material composition as above, but having a crack through a medial internal portion. The workpiece is positioned in the same location within the cavity and irradiated with the same range of frequencies of microwave energy as before. As shown, some of the intrinsic peaks have shifted in frequency and magnitude with respect to FIG. 12. By comparing signature curves at any time during the manufacturing stage, defects can be identified and removed from the production line.

EXAMPLE 7

Figure 14:
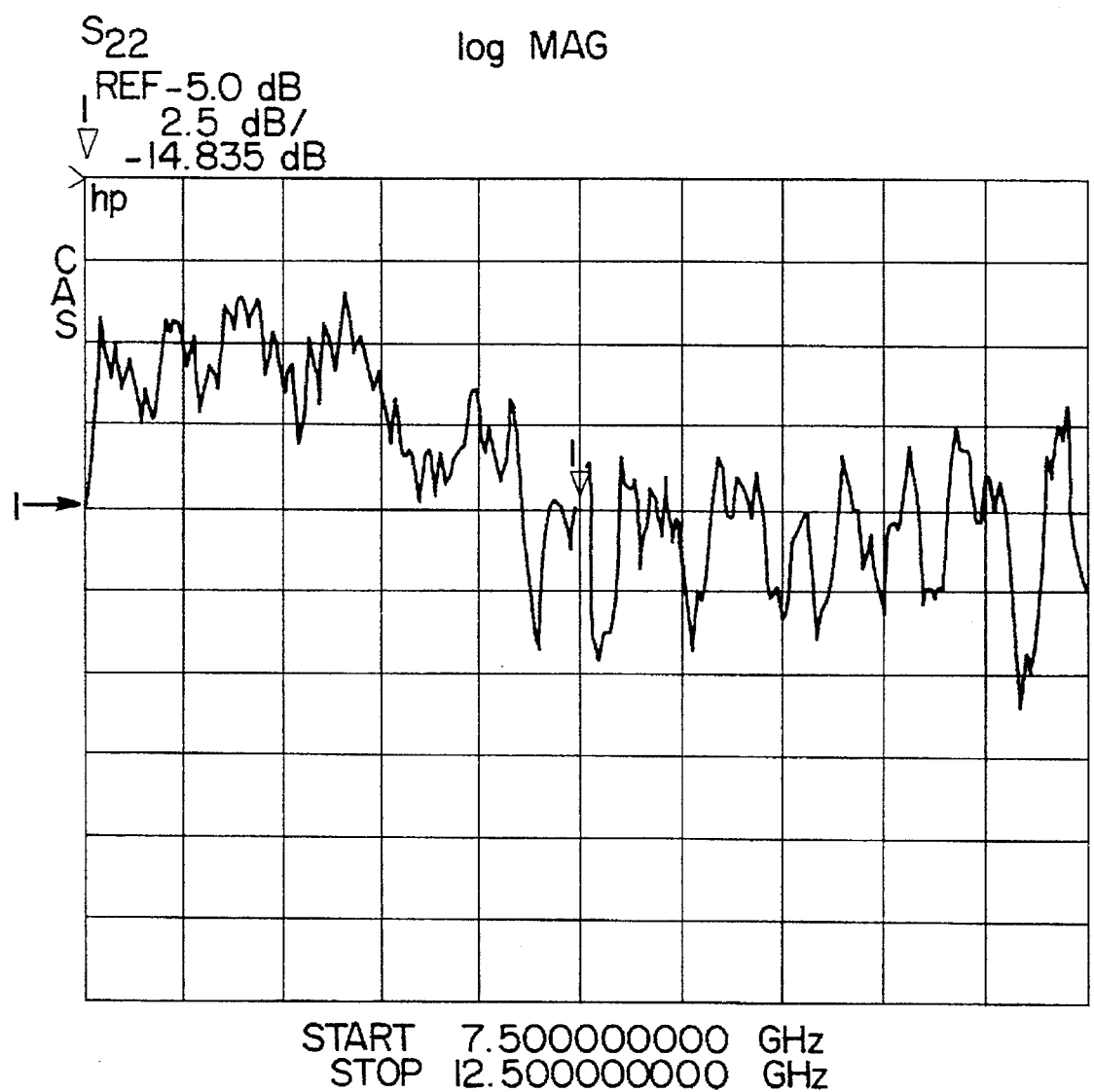
Figure 15:
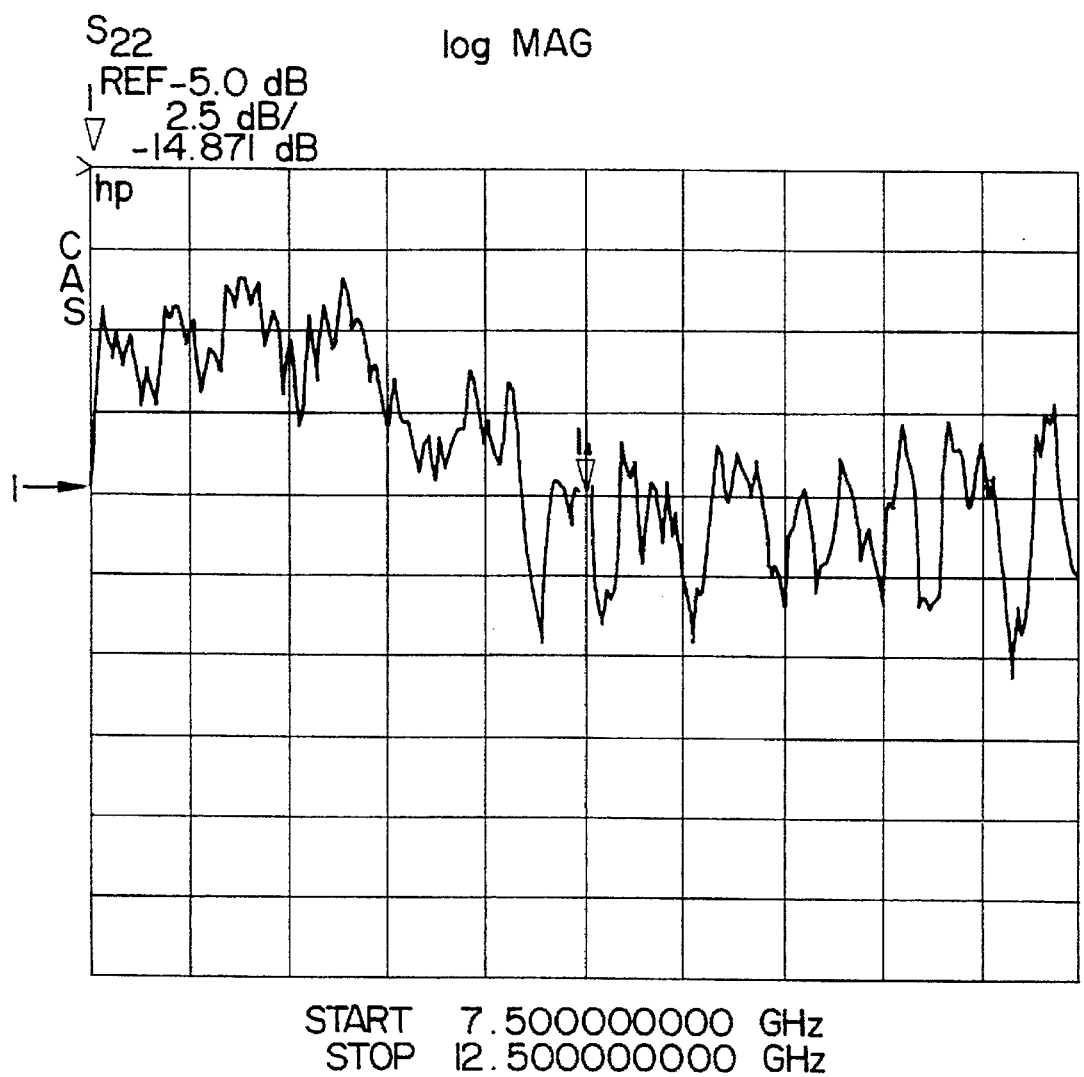

FIG. 14 and FIG. 15 illustrate the effectiveness of the present invention in detecting deviations in material consistency from workpiece to workpiece. FIG. 14 illustrates the signature curve for a unidirectional graphite fiber/epoxy workpiece positioned at the center of the cavity in Example 1, above, and irradiated with the same range of variable frequency microwave energy (7.5 to 12.5 GHz). The workpiece has dimensions of approximately 4.1"×4.1"×0.1". FIG. 15 illustrates the signature curve for a workpiece of the same dimensions and material composition as above, but with moisture entrained at the center. As shown, some of the intrinsic peaks have shifted in frequency and magnitude with respect to FIG. 14. By comparing signature curves, variations in material characteristics can be identified.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A method for monitoring a characteristic of a workpiece, said method comprising the steps of:

positioning the workpiece within a chamber having means for generating variable frequency microwave energy;

sweeping the workpiece with microwave irradiation at a plurality of frequencies;

detecting power reflection for each one of the plurality of microwave frequencies to provide power reflection data; and comparing the power reflection data to a predetermined set of power reflection data.

2. A method according to claim 1, further comprising the step of storing the power reflection data.

3. A method according to claim 1, further comprising the step of generating a signature curve for the workpiece by plotting the power reflection data as a function of microwave frequency.

4. A method according to claim 1, wherein a characteristic of a plurality of workpieces are monitored.

5. A method according to claim 4, further comprising the step of identifying a workpiece having power reflection data that does not fall within an acceptable range of power reflection data.

6. A method according to claim 4, wherein a plurality of different characteristics of a plurality of workpieces are monitored by comparing the power reflection data to a plurality of predetermined sets of power reflection data.

7. A method for processing a workpiece with microwave energy, said method comprising the steps of:

positioning the workpiece within a chamber having means for generating variable frequency microwave energy;

processing the workpiece by sweeping the workpiece with at least one frequency of microwave irradiation; and monitoring a first characteristic of the workpiece during said step of processing.

8. A method according to claim 7, wherein said monitoring step comprises:

detecting power reflection for each one of a plurality of microwave frequencies to provide power reflection data; and comparing the power reflection data to a first predetermined set of power reflection data.

9. A method according to claim 8, further comprising the step of storing the power reflection data.

10. A method according to claim 7, further comprising the step of generating a signature curve for the workpiece by plotting the power reflection data as a function of microwave frequency.

11. A method according to claim 7, further comprising the step of monitoring a second characteristic of the workpiece by comparing the power reflection data to a second predetermined set of power reflection data.

12. A method according to claim 8, further comprising the step of identifying a workpiece having power reflection data that does not fall within an acceptable range of power reflection data.

13. A method according to claim 12, wherein said identifying step is performed during said processing step.

14. A method for monitoring the degree of cure of a resin, said method comprising the steps of:

positioning the resin within a chamber having means for generating variable frequency microwave energy;

sweeping the resin with microwave irradiation at a plurality of frequencies;

detecting power reflection for each one of the plurality of microwave frequencies to provide power reflection data; and comparing the power reflection data to a predetermined set of power reflection data.

15. A method according to claim 14, further comprising the step of storing the power reflection data.

16. A method according to claim 14, further comprising the step of generating a signature curve for the resin by plotting the power reflection data as a function of microwave frequency.

17. A system for microwave processing, said system comprising:

a chamber including means for generating variable frequency microwave energy;

means for positioning a workpiece within said chamber;

means for sweeping the workpiece with a plurality of different microwave frequencies; and means for monitoring a first characteristic of the workpiece.

18. A system according to claim 17, wherein said means for monitoring a first characteristic of the workpiece comprises:

means for detecting power reflection for each one of the plurality of microwave frequencies to provide power reflection data; and means for comparing the power reflection data to a first predetermined set of power reflection data.

19. A system according to claim 18, further comprising means for storing the power reflection data.

20. A system according to claim 18, further comprising means for generating a signature curve for the workpiece by plotting the power reflection data as a function of microwave frequency.

21. A system according to claim 17, comprising means for processing a plurality of workpieces simultaneously.

22. A system according to claim 17, further comprising means for identifying a workpiece having power reflection data that does not fall within an acceptable range of power reflection data.

23. A system according to claim 22, further comprising means for identifying a workpiece having power reflection data that does not fall within an acceptable range of power reflection data during microwave processing of the workpiece.

24. A system according to claim 17, wherein the workpiece comprises a resin and the first characteristic is the degree of cure of the resin.

25. A system according to claim 17, further comprising means for providing real-time feedback control.

* * * * *